US010335636B2

(12) United States Patent
Holma et al.

(10) Patent No.: US 10,335,636 B2
(45) Date of Patent: Jul. 2, 2019

(54) SYSTEM FOR MONITORING PHYSICAL ACTIVITY

(71) Applicant: Polar Electro Oy, Kempele (FI)

(72) Inventors: Veli-Matti Holma, Tyrnava (FI); Taina Koistinen, Ylikiiminki (FI); Petri Jaaskelainen, Oulu (FI); Olli Komulainen, Oulu (FI); Ville Kampman, Oulu (FI); Lotta Ronnberg, Oulu (FI); Mikko Repka, Oulu (FI); Hannu Kinnunen, Oulu (FI); Petteri Siekkinen, Kempele (FI); Tarja Maatta, Kiiminki (FI); Arto Niva, Jaali (FI)

(73) Assignee: Polar Electro Oy, Kempele (FI)

( * ) Notice: Subject to any disclaimer, the term of this patent is extended or adjusted under 35 U.S.C. 154(b) by 402 days.

(21) Appl. No.: 14/398,261

(22) PCT Filed: Sep. 13, 2013

(86) PCT No.: PCT/FI2013/050882
§ 371 (c)(1),
(2) Date: Oct. 31, 2014

(87) PCT Pub. No.: WO2014/207294
PCT Pub. Date: Dec. 31, 2014

(65) Prior Publication Data
US 2016/0256741 A1 Sep. 8, 2016

(51) Int. Cl.
*A63B 24/00* (2006.01)
*A61B 5/00* (2006.01)
(Continued)

(52) U.S. Cl.
CPC ............ *A63B 24/0062* (2013.01); *A61B 5/02* (2013.01); *A61B 5/02438* (2013.01);
(Continued)

(58) Field of Classification Search
CPC . G06F 19/3481; A61B 5/1118; A61B 5/0205; A61B 5/681; A61B 5/02438;
(Continued)

(56) References Cited

U.S. PATENT DOCUMENTS

2008/0275309 A1* 11/2008 Stivoric ................. A61B 5/411
600/300
2010/0216601 A1* 8/2010 Saalasti ................. A61B 5/024
482/8
(Continued)

FOREIGN PATENT DOCUMENTS

EP        2 631 830 A2    8/2013
WO    2011072111 A2     6/2011

OTHER PUBLICATIONS

International Search Report, Application No. PCT/FI2013/050882, dated Jun. 25, 2014, pp. 1-9.
(Continued)

*Primary Examiner* — Jack Yip
(74) *Attorney, Agent, or Firm* — FisherBroyles, LLP

(57) ABSTRACT

A system that monitors user activity includes a wrist device including a curved body and an electronic circuitry supported by the body. The electronic circuitry includes a first set of light emitting diodes arranged in a matrix form and forming a display unit, at least one motion sensor configured to measure physical motion caused by a user to the wrist device, and at least one processor configured to acquire motion measurement data from the at least one motion sensor, to process the motion measurement data into a motion activity metric, and to cause the display unit to display the motion activity metric. The at least one processor is further configured to acquire heart activity measurement data from a heart activity sensor, to process the heart activity
(Continued)

measurement data into a heart activity metric, and to cause the display unit to display the heart activity metric.

20 Claims, 10 Drawing Sheets

(51) Int. Cl.
  *A61B 5/024* (2006.01)
  *A61B 5/11* (2006.01)
  *G06F 19/00* (2018.01)
  *H04M 1/725* (2006.01)
  *A61B 5/02* (2006.01)
  *A61B 5/103* (2006.01)
  *G09B 19/00* (2006.01)

(52) U.S. Cl.
  CPC ............. *A61B 5/103* (2013.01); *A61B 5/11* (2013.01); *A61B 5/1118* (2013.01); *A61B 5/4866* (2013.01); *A61B 5/681* (2013.01); *A61B 5/742* (2013.01); *G06F 19/3481* (2013.01); *G09B 19/0038* (2013.01); *H04M 1/7253* (2013.01); *H04M 2250/02* (2013.01); *H04M 2250/12* (2013.01)

(58) Field of Classification Search
  CPC ......... A61B 5/742; A61B 5/11; A61B 5/4866; A61B 5/02; A61B 5/103; A63B 24/0062; G09B 19/0038; H04M 1/7253; H04M 2250/02; H04M 2250/12
  USPC ........................................................ 434/247
  See application file for complete search history.

(56) References Cited

U.S. PATENT DOCUMENTS

| | | | |
|---|---|---|---|
| 2011/0257496 A1* | 10/2011 | Terashima | G06F 19/00 600/347 |
| 2011/0275940 A1* | 11/2011 | Nims | A61B 5/222 600/483 |
| 2012/0083705 A1 | 4/2012 | Yuen et al. | |
| 2012/0149996 A1* | 6/2012 | Stivoric | A61B 5/01 600/301 |
| 2012/0253485 A1 | 10/2012 | Weast et al. | |
| 2012/0283855 A1* | 11/2012 | Hoffman | G01C 21/20 700/91 |
| 2012/0326873 A1* | 12/2012 | Utter, II | G06F 3/016 340/573.1 |
| 2013/0002435 A1* | 1/2013 | Utter, II | A61B 5/0022 340/575 |
| 2013/0006124 A1* | 1/2013 | Eyal | A61B 5/024 600/483 |
| 2013/0072765 A1 | 3/2013 | Kahn et al. | |
| 2013/0106684 A1 | 5/2013 | Weast et al. | |
| 2013/0178754 A1 | 7/2013 | Rulkov et al. | |
| 2014/0085077 A1* | 3/2014 | Luna | G08B 6/00 340/539.11 |
| 2014/0135594 A1 | 5/2014 | Yuen et al. | |
| 2014/0235166 A1* | 8/2014 | Molettiere | H04B 7/26 455/41.2 |
| 2014/0288680 A1* | 9/2014 | Hoffman | G06K 9/00342 700/91 |
| 2016/0270717 A1* | 9/2016 | Luna | A61B 5/7246 |

OTHER PUBLICATIONS

Supplementary European Search Report, EP 13 88 8382, 2 pages, dated Mar. 16, 2017.

* cited by examiner

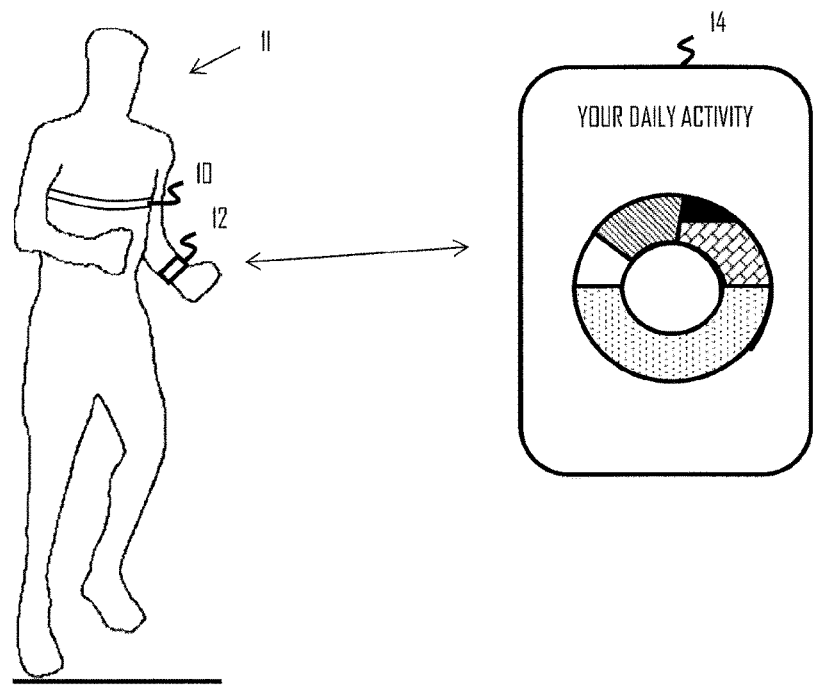
Fig 1
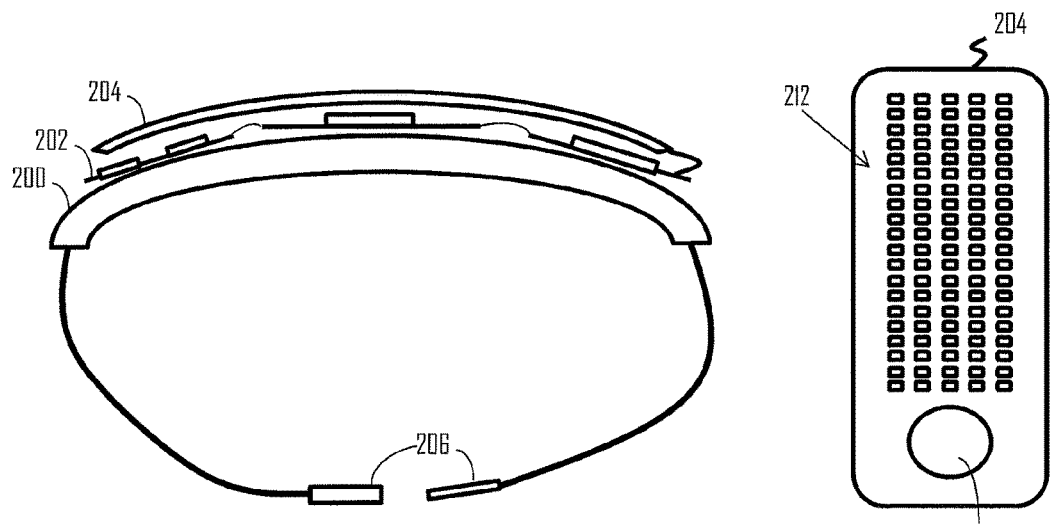
Fig 2A
Fig 2B

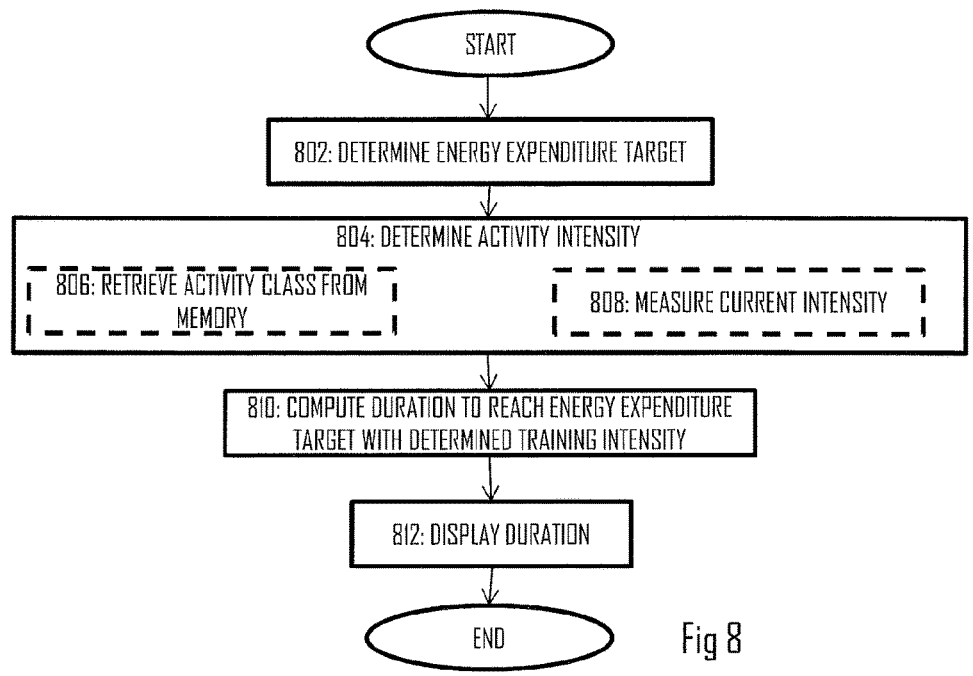
Fig 8
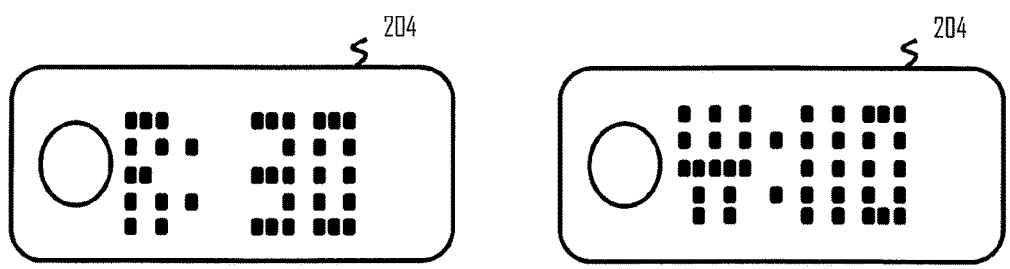
Fig 9A                    Fig 9B

SYSTEM FOR MONITORING PHYSICAL ACTIVITY

CROSS-REFERENCE TO RELATED APPLICATION

This application is a National Stage application of International Application No. PCT/FI2013/050882, filed Sep. 13, 2013, which is incorporated by reference herein in its entirety.

BACKGROUND

Field

The invention relates to the field of sensor devices and, particularly, to a system for monitoring physical activity of a user.

Description of the Related Art

Motion sensors may be used to measure an activity level of a user when attached to the user's body.

SUMMARY

According to an aspect, there is provided a system for monitoring user activity, comprising: a wrist device comprising a curved body and an electronic circuitry supported by the body, the electronic circuitry comprising a first set of light emitting diodes arranged in a matrix form and forming a display unit, at least one motion sensor configured to measure physical motion caused by a user to the wrist device, a heart activity sensor based on optical heart activity sensing, and at least one processor configured to acquire motion measurement data from the at least one motion sensor, to process the motion measurement data into a motion activity metric, and to cause the display unit to display the motion activity metric, wherein the at least one processor is further configured to acquire heart activity measurement data from the heart activity sensor, to process the heart activity measurement data into a heart activity metric, and to cause the display unit to display the heart activity metric.

Embodiments of the invention are defined in the dependent claims.

BRIEF DESCRIPTION OF THE DRAWINGS

Embodiments of the present invention are described below, by way of example only, with reference to the accompanying drawings, in which FIG. 1 illustrates an activity monitoring system according to an embodiment of the invention;

FIGS. 2A to 2D illustrate some embodiments of a wrist device comprised in the activity monitoring system;

FIG. 8 illustrates a flow diagram of a process for instructing a user of the wrist device to reach activity targets according to an embodiment of the invention;

FIGS. 9A and 9B illustrate display views to be displayed in connection with the process of FIG. 8;

DETAILED DESCRIPTION

Figures 2C, 2D:
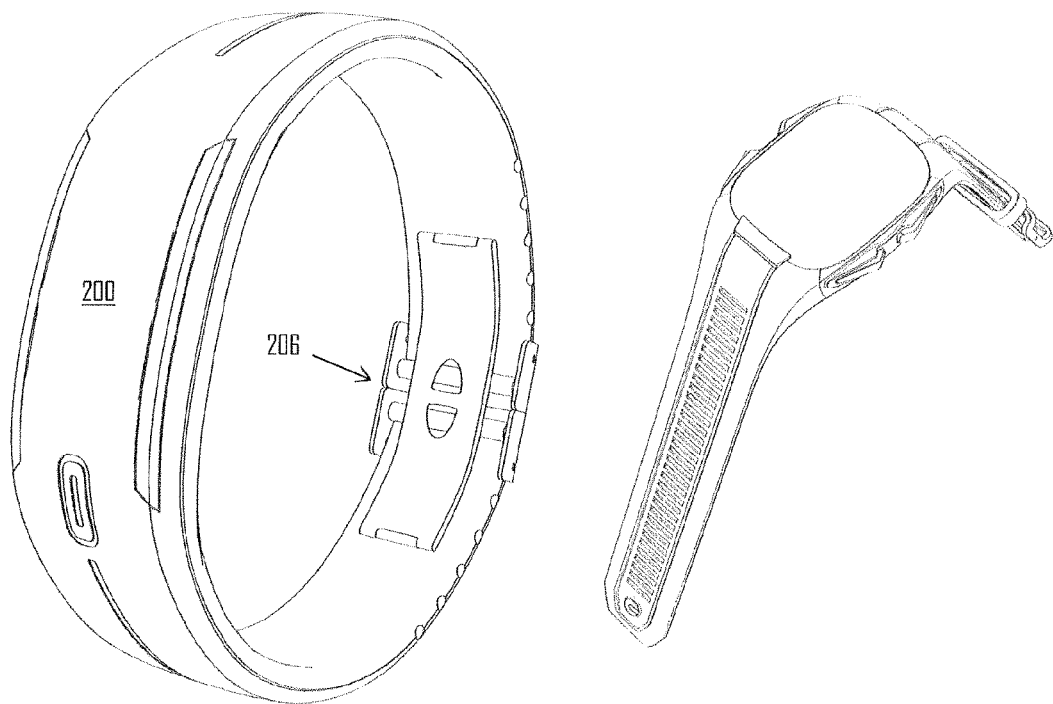

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

FIG. 1 illustrates a physical training environment to which embodiment of the invention may be applied. FIG. 1 illustrates an activity monitoring system comprising an activity monitoring apparatus 12 comprising a simplified user interface and a portable electronic device 14 comprising a user interface with more features. The activity monitoring system may further comprise one or more external sensor devices 10 such as a heart rate transmitter, a stride sensor, a positioning sensor, etc. Referring to FIG. 1, a user 11 may carry an activity monitoring apparatus 12. The activity monitoring apparatus may be a portable or wearable device such as a wrist device 12. The wrist device 12 may comprise at least one motion sensor configured to measure motion induced by the user 11 to the wrist device 12 by moving a hand in which the user 11 wears the wrist device 12.

In an embodiment, the motion sensor(s) comprise at least one of the following: an accelerometer, a magnetometer, and a gyroscope.

In an embodiment, the motion sensor comprises an accelerometer and a gyroscope. The motion sensor may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion sensor comprises a gyroscope and a magnetometer. The motion sensor may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

The portable electronic device 14 may be a mobile phone, a smart phone, a palm device, a tablet computer, or a portable digital assistant. The portable electronic device 14 and the wrist device 12 may be configured to establish a wireless communication connection with one another and exchange activity data over the wireless communication connection. The wireless communication connection may be established according to Bluetooth® specifications, e.g. Bluetooth Low Energy. The activity monitoring system may employ the simplified user interface of the wrist device 12 to display coarse activity information and the sophisticated user interface of the portable electronic device to display the activity information in a higher display resolution. In an embodiment, the portable electronic device 12 comprises a communication circuitry configured to establish the wireless communication connection with a communication circuitry of the wrist device, a display screen, and at least one processor configured to receive at least one of motion measurement data and heart activity measurement data from the wrist device through the communication circuitry, to process the received measurement data, and to cause the display screen to display the processed measurement data.

In an embodiment, the motion measurement data characterizes the physiological activity of the user.

In an embodiment, the motion measurement data comprises acceleration values in at least one dimension selected from the x-, y-, and x-axis presented in the acceleration sensor-fixed or in a reference coordinate system. The reference coordinate system may be fixed to a gyroscope or magnetometer coordinate systems, and the motion measurement data may be mapped to the reference coordinate system.

In an embodiment, the motion measurement data comprises pulse data determined from at least one acceleration values selected from selected from the x-, y-, and x-axis presented in the acceleration sensor-fixed or in a reference coordinate system.

In an embodiment, the motion measurement data comprises time distribution spent on at least one motion intensity zone, where the motion intensity may derived from at least one of acceleration values or motion pulse frequency. Below, the motion intensity zone maps to activity classes in some aspects.

In an embodiment, the motion measurement data characterizes the mechanical impact of the motion to the human body. The mechanical impact may also be referred to as mechanical training load, which characterizes the mechanical muscular load of an exercise.

In an embodiment, the heart activity measurement data characterizes cardiovascular activity of the user.

In an embodiment, the heart activity measurement data comprises heart beat intervals of the heart beats, e.g. R-R intervals.

In an embodiment, the heart activity measurement data comprises heart rate values, which may or not may be averaged over a time period.

In an embodiment, the heart activity measurement data characterizes the user's energy expenditure rate or energy expenditure derived from heart rate or heart beat intervals.

In an embodiment, the heart activity measurement data characterizes time distribution spent on at least one heart rate zone having a lower limit and an upper limit.

In an embodiment, the heart activity measurement data characterizes the training load of the exercise or motion to the user's body. The training load may comprise a loading component which characterizes the physiological load of the motion and a recovery component which characterizes the user's body's trend to recover towards a normal physiological state after the motion or an exercise.

Additionally, the more versatile input interface of the portable electronic device 14 may be used by the user to control the activity monitoring relating to the motion measurement data and the heart activity measurement data, and the portable electronic device 14 may transmit commands and configuration parameters to the wrist device over the wireless communication connection.

Let us now describe an embodiment of the wrist device 12 with reference to FIGS. 2A and 2B. The wrist device 12 may comprise a curved body 200 and an electronic circuitry 202 supported by the curved body 200. The body may be flexible, semi-rigid or rigid. The electronic circuitry 202 may comprise a first set of light emitting diodes (LED) 212 arranged in a matrix form and forming a display unit. The electronic circuitry 202 may further comprise at least one motion sensor configured to measure physical motion caused by a user to the wrist device 12. The electronic circuitry 202 may further comprise the above-mentioned communication circuitry configured to provide the wrist device with wireless communication capability. The electronic circuitry 202 may further comprise at least one processor configured to acquire motion measurement data from the at least one motion sensor, to process the motion measurement data into an activity metric, and to cause the display unit 212 to display the activity metric. In an embodiment, the at least one processor is further configured to acquire heart activity measurement data from a heart activity sensor, to process the heart activity measurement data, and to output the processed heart activity measurement data to at least one of the display unit 212 and the communication circuitry.

FIG. 2A illustrates the structure of the wrist device 12, while FIG. 2B illustrates a user interface of the wrist device 12. Referring to FIG. 2A, the wrist device 12 may have a layered sandwich structure wherein the curved body 200 forms a support layer and protection for a layer of the electronic circuitry 202 and a user interface layer 204 comprising the LED display 212. The body 200 may be rigid. The body 200 may comprise one or more recessions to house the electronics, such as the electronic circuitry 202 and a battery. The curvature of the curved body 200 may be designed according to a shape of an average wrist or arm. The curved body 200 may be semiannular or semioval as shown in FIG. 2A or even annular, depending on the design. In some embodiments, the curved body 200 may form a continuous annular or oval ring but, in other embodiments, the curved body 200 comprises two ends 206 to which a locking mechanism may be disposed. The purpose of the locking mechanism may be to facilitate the removal of the wrist device 12 and attach the wrist device 12 more firmly to the wrist. A cross-section of the curved body 200 may be U-shaped and open upwards, e.g. away from the wrist, to house the electronic circuitry 202.

The electronic circuitry 202 may comprise a plurality of printed wiring boards (PWB) connected together by flexible electronic connectors. As a consequence, the electronic circuitry 202 may be accommodate the curved shape of the curved body 200 and yet have the mechanical durability of the rigid PWB. The processor, the communication circuitry, and the motion sensor(s) may be arranged on the electronic circuitry 202. The rigid body 200 may comprise a through hole to which a wired connector of the electronic circuitry 202 may be disposed. The wired connector may be connected to the communication circuitry configured to support wired connections as well. The wired connection may be realized according to specifications of a Universal Serial Bus, for example, and the wired connection may enable connecting the wrist device to a personal computer (PC). In other embodiments, the wired connector may be provided at another location in the wrist device, e.g. in the locking mechanism 206. In such a case, a wiring may be provided between the communication circuitry and the wired connector in or on the curved body 200.

The user interface layer 204 may be disposed on top of the layer comprising the electronic circuitry 202, and the layers may be connected by a flexible connector at an end of the user interface layer 204. A cover may be disposed on top of the user interface layer 204 to protect the electronic circuitry 202.

FIG. 2B illustrates an embodiment of the user interface layer 204. The user interface layer 204 may comprise a matrix of light emitting diodes (LEDs) 212. In an embodiment, the size of the LED matrix 212 may be 5×20, i.e. five LEDs in a row and 20 LEDs in a column. Other sizes are equally possible but the resolution of the LED matrix 212 may be lower than a resolution of a thin-film transistor (TFT) display of the same size. As a consequence, power consumption is reduced by providing a simple, low-resolution display. In an embodiment, the display contains 100 or less pixels. In another embodiment, the display contains 120 or less pixels, and in yet another embodiment the display contains 150 or less pixels. Each LED indicator in the LED matrix may be designed to illuminate in one or more colours.

The user interface layer 204 may comprise a user input device 210. In an embodiment, the user input device 210 comprises or consists of a single button. The button may be a multi-function button having multiple control modes. In an embodiment, the button is sensitive to touch through capacitive coupling.

FIGS. 2C and 2D illustrate detailed perspective views of some embodiments of the wrist device. The embodiment of FIG. 2C is a bracelet type of wrist device having an annular curved body 200 having a cut for a locking mechanism. The locking mechanism 206 may be used to attach/remove the bracelet to/from a wrist of the user. The bracelet type of wrist device may employ the motion sensing and heart activity monitoring features. A wrist watch type of wrist device illustrated in FIG. 2D may employ further features, e.g. at least one of the following: positioning through an internal or external positioning sensor (based on Global Positioning System or, in general, a Global Navigation Satellite System), bicycling measurements via wireless communication with sensors attached to a bicycle (force sensor or a cadence sensor), and ambient measurements such as air pressure, temperature, and/or humidity measurements through external or internal sensors.

As described above, the wrist device may communicate with one or more external sensors. The communication may be based on a wireless communication technology such as Bluetooth®, e.g. Bluetooth Low Energy. In an embodiment, the wireless communication technology is ANT or ANT0 by Dynastream, or UWB (Ultra Wide Band). Pairing the wrist device with a sensor, e.g. a heart activity sensor, and establishing a wireless communication link may be carried out according to an embodiment illustrated in a flow diagram of FIG. 3.

Figure 3:
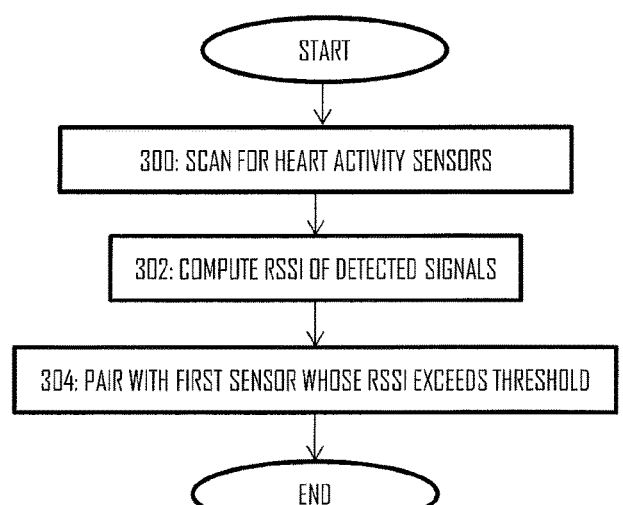
FIG. 3 illustrates a flow diagram of a process for pairing the wrist device with a sensor device according to an embodiment of the invention.

Referring to FIG. 3, the wrist device scans for heart activity sensors or, in general, sensors in block 300. The wrist device may execute block 300 constantly, or the execution of block 300 may be triggered by a user input, e.g. an input through the input device of the wrist device or by detecting a determined motion trajectory with the motion sensor(s) of the wrist device. The motion trajectory may be a trajectory of bringing a user's wrist to touch a user's chest. In connection with scanning in block 300, the wrist device may carry out a master role in a Bluetooth inquiry procedure, e.g. it may transmit an inquiry request to which any idle sensor within the coverage area responds. The user may activate a sensor to carry out scanning for the wrist devices. For example, a heart activity sensor may be activated by placing its electrodes in contact with the user's skin. The wrist device may then receive and process the responses. The response may identify the responding sensor and, on the basis of such identifiers, the wrist device may rule out sensors with which it is not configured to pair.

In block 302, the wrist device measures a received signal strength indicator (RSSI) of the responses it has received. The RSSI may be any metric indicating received signal strength or power. The wrist device may compare the measured RSSIs with a threshold level and initiate pairing upon detecting that an RSSI exceeds the threshold. The pairing may be initiated immediately upon detecting that RSSI exceeds the threshold, and the remaining RSSIs may be omitted from the comparison. In an embodiment, the pairing process excludes user interaction through the user interface of the wrist unit. The threshold may be set to be sufficiently high so that only sensors at a predefined proximity from the wrist device are able to send a signal that exceeds the threshold. Accordingly, setting the threshold to be sufficiently high, proximity detection and associated pairing may be enabled. For example, when the pairing is intended to be carried out by the user placing the wrist device into a contact or at least close proximity to the sensor device, the threshold may be set such that the wrist device is able to receive the signal sent by the sensor device such that the threshold is exceeded only when the two devices are in each other's predefined proximity.

In an embodiment, upon pairing with a sensor device, the wrist device is configured to prevent pairing with any other sensor device. A new pairing with another sensor device may be allowed when the current pairing is terminated or disconnected.

In an embodiment, the predefined proximity is less than 20 cm.

In an embodiment, the predefined proximity is less than 10 cm.

In an embodiment, the predefined proximity is less than 5 cm.

In an embodiment, the predefined proximity is less than 2 cm.

In an embodiment, the predefined proximity is less than 1 cm.

In an embodiment, upon detecting multiple sensor devices, the wrist device may choose to pair to a sensor device with which a previous pairing was performed, provided that such a sensor device has been detected. If the previously-paired sensor device(s) has not been detected, the process of FIG. 3 may be followed.

In an embodiment, the wrist device is configured to operate in a motion monitoring mode when the communication circuitry is not connected to an external heart activity sensor. In the motion monitoring mode, the wrist device 12 measures and processes motion measurement data and displays associated motion activity metrics.

In an embodiment, the wrist device 12 is configured to operate in a heart activity monitoring mode when the communication circuitry is connected to the external heart activity sensor. In the heart activity monitoring mode, the wrist device 12 receives and processes heart activity measurement data and displays associated heart activity metrics. The wrist device 12 may or may not process and display motion activity metrics during the heart activity monitoring mode.

In an embodiment, the wrist device 12 detects the external heart activity sensor and automatically changes from the motion monitoring mode to the heart activity monitoring mode. The detection may be based on the completion of the pairing process between the wrist device 12 and the heart activity sensor. In an embodiment, no user interaction is required when changing between the motion monitoring mode and the heart activity monitoring mode.

In an embodiment, the wrist device changes from the heart activity monitoring mode to the motion monitoring when the pairing between the wrist device 12 and the external heart activity sensor is undone.

In an embodiment, the wrist device 12 changes from the heart activity monitoring mode to the motion monitoring when the wrist device 12 detects heart activity less than a predetermined threshold.

In an embodiment, the wrist device 12 changes from the heart activity monitoring mode to the motion monitoring when the wrist device 12 detects an indication of cardiac inactivity from the external heart activity sensor. The cardiac inactivity may be indicated with a predefined heart activity data structure or separate stop bits in the data transfer protocol.

Figure 4:
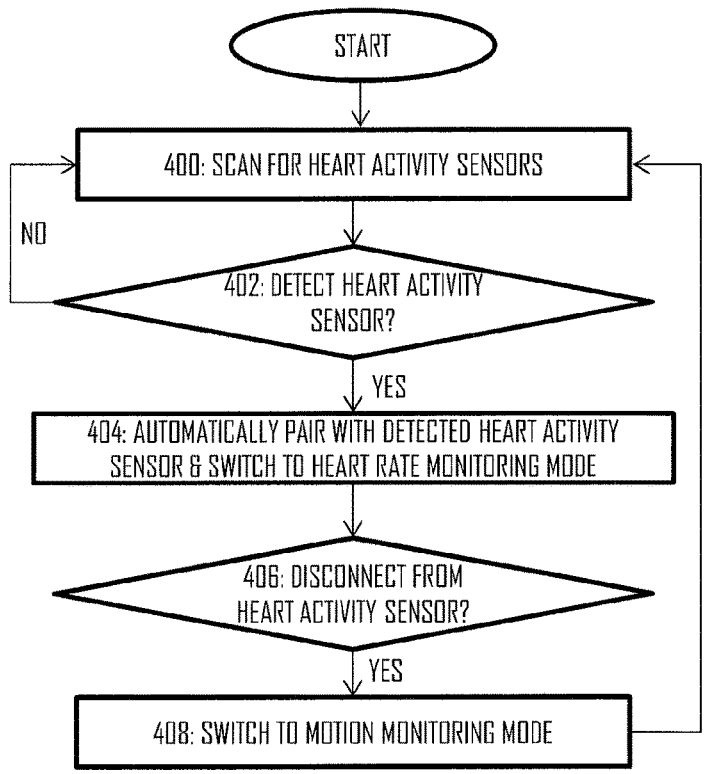
FIG. 4 illustrates a flow diagram of a process for changing an operational mode of the wrist device according to an embodiment of the invention.

FIG. 4 illustrates a flow diagram of a process for changing the modes automatically in the wrist device. Referring to FIG. 4, the wrist device scans for the heart activity sensors in block 400. In block 402, the wrist device determines whether or not it has detected a heart rate sensor with which to pair. In an embodiment, block 402 comprises the above-described comparison with the threshold. If no heart activity sensors are found for pairing, the process may return to block 400. If the heart activity sensor for pairing is detected in block 402, the wrist device initiates the pairing and establishes a connection with the selected heart activity sensor. When the communication link has been established, the wrist device changes its operational mode to a heart activity monitoring mode (block 404). In this mode, the wrist device may receive heart activity measurement signals wirelessly from the heart activity sensor and produce one or more into heart activity metrics. The one or more heart activity metrics may comprise a heart rate, energy consumption, heart rate accumulation over time, or an activity class.

An activity class may represent quantization of the motion activity metric and/or heart activity metric. The range of motion activity metrics and/or heart activity metrics may be divided into a plurality of zones, and each zone may represent an activity class. Lowest motion activity metrics and/or heart activity metrics may be allocated to the lowest activity class and vice versa.

The heart activity monitoring mode may be maintained as long as the wrist device is paired with the heart activity sensor. Upon disconnecting the wireless connection (block 406), the wrist device may switch to a motion monitoring mode in which it computes the motion activity metric(s) on the basis of the motion measurement data. The motion activity metric(s) may comprise at least one of the following: an activity class, activity accumulation over time, and energy consumption. When the wrist device has disconnected, it may return to block 400 and maintain the motion monitoring mode until it detects a heart activity sensor for new pairing on the basis of the scanning carried out in block 400.

Figures 5A, 5B:
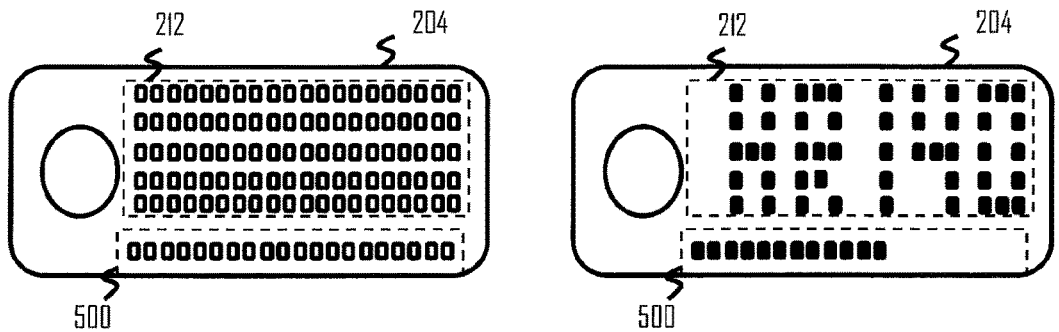
FIGS. 5A and 5B illustrate a display unit of the wrist device according to an embodiment of the invention.

FIGS. 5A and 5B illustrate another embodiment of the user interface layer 204. In this embodiment, the user interface layer 204 comprises the LED matrix 212 as a primary display, and the user interface layer 204 further comprises a secondary display 500 visually separated from the primary display 212. The secondary display 500 may be realized by a row of LED indicators, as shown in FIGS. 5A and 5B. One of the displays 212, 500 may be configured to display the heart activity metric and the other of the displays 212, 500 may be configured to display the motion activity metric. Referring to FIG. 5B, the primary display 204 may be configured to display the heart activity metric in the form of characters. The secondary display 500 may be configured to illustrate the motion activity metric as a bar with the number of illuminated LED indicators being proportional to the current degree of activity. In another embodiment of FIG. 5B, both the primary display 212 and the secondary display 500 may be configured to illustrate the heart activity metric or the motion activity metric. For example, the heart activity may be illustrated with characters and with a bar such that the number of illuminated LED indicators indicates how close to a target heart activity the user performs at the moment. A target may be heart activity producing the illumination of no LED indicators or all LED indicators on the secondary display, depending on the design. Similarly, the motion activity metric may be illustrated with characters, e.g. by an activity class index, and with a bar such that the number of illuminated LED indicators indicates how close to a target motion activity the user performs at the moment. As a consequence, the primary display may be used an information source of the current absolute performance and the secondary display may be used as a training or activity guidance tool for instructing the user to meet the target activity.

The primary display may be configured to display different types of information in the characters formed by illuminating selected individual LED indicators. In an embodiment, the secondary display 500 is configured to illustrate a cumulative motion activity metric illustrating accumulation of activity over a determined time period. In an embodiment, the secondary display 500 is configured to illustrate a momentary motion activity metric descriptive of a current activity level or an activity class. The momentary motion activity metric may illustrate activity over a significantly shorter time period than the cumulative motion activity metric. In an embodiment, the secondary display 500 is configured to illustrate a total exertion load computed from accumulation of at least one of the motion activity metric and the heart activity metric. The computation of the total exertion load may take into account recovery gained during inactive periods. In an embodiment, the secondary display 500 is configured to illustrate a cumulative heart activity metric illustrating accumulation of heart activity during a determined time period. In an embodiment, the secondary display 500 is configured to illustrate a momentary heart activity metric descriptive of a current activity level or an activity class. The momentary heart activity metric may illustrate activity over a significantly shorter time period than the cumulative heart activity metric. In an embodiment, the secondary display 500 is configured to illustrate an energy expenditure value descriptive of energy expenditure accumulation of a determined time period or a momentary energy expenditure value. The momentary expenditure value may illustrate energy expenditure over a significantly shorter time period than the cumulative energy expenditure value.

As described above, the pixels of the secondary display 500 may be configured to illuminate in different colours. Each colour may be associated with a different indicator, e.g. the heart activity metric(s) may be illustrated with one colour and the motion activity metric(s) may be illustrated with another colour. Other distinguishing illustration methods may be used, e.g. blinking the LED indicators with one or more frequencies. For example, the heart rate may be illustrated with one or more blinking or pulsing LED indicators that pulse with the same frequency as the user's current heart rate.

Figure 6:
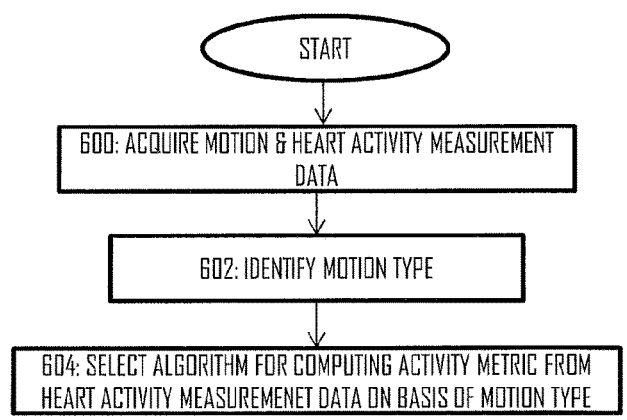
FIG. 6 illustrates a flow diagram of a process for using both motion measurement data and heart activity measurement data according to an embodiment of the invention.
Figure 7:
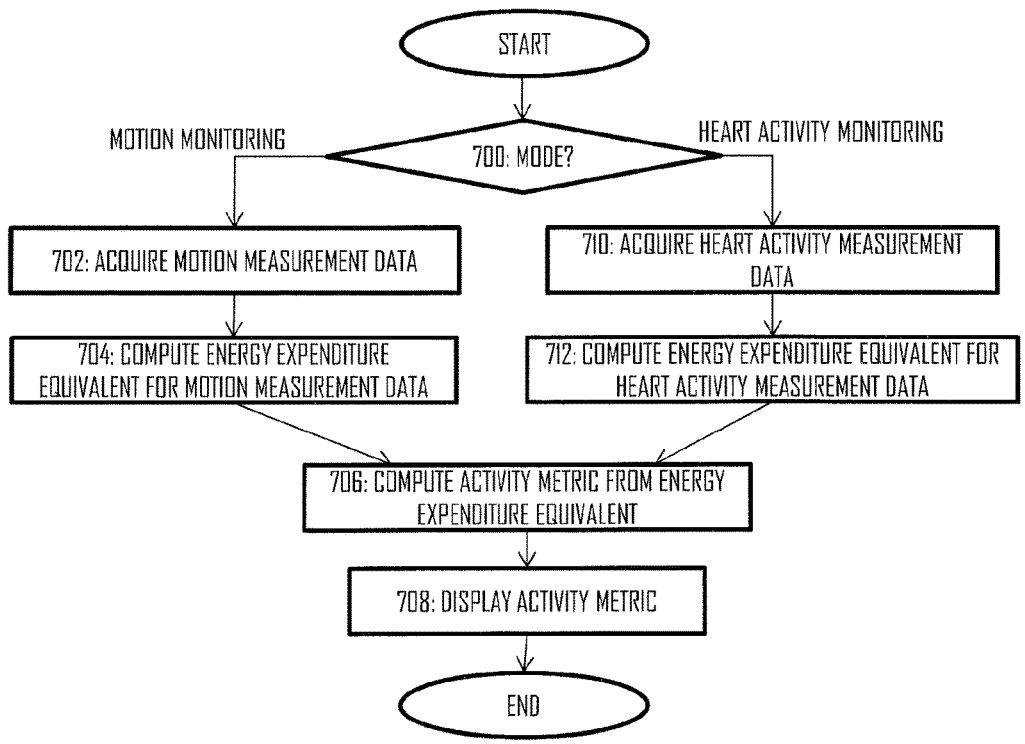
FIG. 7 illustrates a flow diagram of a process for mapping heart activity measurement data and motion measurement data into a common scale according to an embodiment of the invention.

In an embodiment, an activity metric is computed by using both motion measurement data and heart activity measurement data. FIGS. 6 and 7 illustrate flow diagrams of such procedures. Referring to FIG. 6, the wrist device acquires the motion measurement data and the heart activity measurement data from internal and/or external sensors in block 600. In block 602, the wrist device processes the motion measurement data and determines motion type from the motion measurement data. Different motion types are typically associated with different motion trajectories that may be represented by reference motion data associated with each motion type and stored in a memory of the wrist device. The wrist device may compare the motion measurement data with the reference motion data and determine the motion type associated with reference motion data that matches with the motion measurement data. The motion measurement data and the reference motion data may be presented in the accelerometer-fixed or gyroscope/magnetometer-fixed reference coordinate system described above. Block 602 may comprise identifying at least one of the following motion types: walking, sitting, standing still, sleeping, and exercising. The exercising may comprise at least one of the following sub-types: running, swimming, bicycling, climbing, rowing, and weight lifting. Upon identifying the motion type, the wrist device may select a corresponding algorithm for computing the heart activity metric (block 604). The memory may store mappings between sports type and associated heart activity measurement data processing algorithms. Upon selecting the appropriate algorithm, the wrist device may compute the heart activity metric from the heart activity measurement data with the selected algorithm. By using sports-type-related activity computation, more accurate activity estimates are acquired. For example, having an increased heart rate resulting from sitting and watching a horror movie has completely different physiological effect than that caused by high heart rate in running. As a consequence, a better estimate of real physical activity may be acquired.

In an embodiment, the wrist device 12 is configured to estimate a sleep index characterizing the sleep quality and the sleep time by using an activity sensor, such as an accelerometer.

In an embodiment, a sleeping time is defined as a continuous time when the motion measurement data indicates instantaneous physical activity below a predefined sleep threshold. In an embodiment, the sleep time is expressed in time unit, such as hours and minutes.

In an embodiment, the sleep quality is defined as a relative number of deep sleep time periods of predefined length compared to total number of predefined time periods during the sleep time. In an embodiment, a time window falls into a deep sleep category, when the physical activity obtained from the motion measurement data stays below a predefined deep sleep threshold. If the motion measurement data exceeds the deep sleep threshold and stays below the sleep threshold, the time period is deemed to express restless sleep. In an embodiment, the deep sleep threshold is one detected pulse with a predefined pulse detection threshold. The pulse detection threshold depends on the mechanical and electronic implementation of the wrist device 12.

As an example, let us assume that the total sleeping time is 8 hours (480 mins). Let us also assume that the predefined length of the deep sleep time period is 2 mins. The 8-hour sleep time comprises 240 time periods of 2 min length. Let us further assume that the wrist unit 12 detected 24 time periods of 2 min length with restless sleep. This indicates that 10% of the sleep time periods were deemed to be restless, and thus 90% of the sleep time was good sleep. In this case, the sleep index would be 0.9 or 90%.

FIG. 7 illustrates an embodiment where the wrist device 12 estimates the physical activity from the motion measurement data in some time interval and from the heart activity measurement data in other time intervals. Activity computed in this manner by using various measurement data is then illustrated by using one activity indicator in the display. The embodiment of FIG. 7 provides a procedure for mapping the activity estimates resulting from the different measurement data on a common scale. This is achieved through an intermediate metric. The intermediate metric may be energy expenditure equivalent. Referring to FIG. 7, the operational mode of the wrist device is determined in block 700. If the wrist device operates in the motion monitoring mode, the wrist device acquires the motion measurement data in block 702 and computes energy expenditure from the motion measurement data (block 704). This may be carried out by using state-of-the-art energy consumption computation algorithms. For example, an integral of acceleration measurement data provides a distance metric which may be mapped to energy expenditure with sufficient background information, e.g. the user's age, weight, and gender. The determined energy expenditure is then mapped to an activity metric by using a predetermined mapping function (block 706), and the activity metric is displayed in block 708. Similarly, when the operational mode of the wrist device is the heart activity monitoring mode, the wrist device acquires the heart activity measurement data in block 710 and computes energy expenditure from the heart activity measurement data (block 712). This may be carried out by using state-of-the-art energy consumption computation algorithms. For example, the heart rate values may be mapped to the energy expenditure through the known maximum oxygen uptake ($VO_2$ max) of the user. The determined energy expenditure is then mapped to an activity metric by using the predetermined mapping function (block 706), and the activity metric is displayed in block 708.

Accordingly, a common activity metric may be computed in multiple operational modes of the wrist device and the same exercise profiles or activity targets may be used regardless of the type of measurement data available to the wrist device. The embodiment of FIG. 7 may be easily expanded to other measurement data as well, e.g. bicycling measurement data such as cycling power measurement data or cycling cadence measurement data.

In an embodiment, the embodiment of FIG. 6 is executed in block 712.

In an embodiment, activity targets may be programmed to the wrist device. The activity and activity target relates to motion activity, heart activity or both. The activity may relate to, for example, intensity or time spent on at a given intensity range. In an embodiment, the activity is a measure for accumulated activity. In an embodiment, activity characterizes physiological energy expenditure also referred to as energy consumption.

An activity target may be set for a determined time interval such as a daily target activity, a weekly target activity, or a monthly target activity. The wrist device may then illustrate on the display instructions as how to reach the target. FIG. 8 illustrates a process for determining the target and instructing the user as how to reach the target. FIGS. 9A and 9B illustrate embodiments of display content the wrist device may display as the instructions. Referring to FIG. 8, the wrist device may determine an energy expenditure target in block 802. The activity targets may be measured through the energy expenditure. Block 802 may determine a total energy expenditure target for a determined time interval and subtract energy expenditure already accumulated from that total energy expenditure, thus acquiring a remaining energy expenditure that should be accumulated. In block 804, one or more training intensities are determined. In an embodiment, one or more activity intensity classes are retrieved from a memory of the wrist device (block 806). The intensity classes may represent different degrees of activity such that the higher activity is associated with higher energy consumption or other accumulated physiological measure. In another embodiment, a current training intensity as represented by the latest motion measurement data and/or the heart activity measurement data is computed (block 808). The current training intensity may be quantized to the activity classes, or it may be used as such. The activity classes may comprise at least one of the following: running, walking, standing still, sitting, and cycling.

In an embodiment, the training intensity is characterized by an energy expenditure rate, expressed in kcal/min or kcal/s or MET (Metabolic equivalent=kcal/(kg*h) h=hours).

In block 810, time duration to reach the energy expenditure target (determined in block 802) with the intensities (determined in block 804) is computed. In other words, block 810 may comprise computing how long the user has to exercise at the determined activity level to reach the target. Block 810 may be computed for each intensity and/or activity class determined in block 804. The determined durations may then be displayed to the user in block 812. FIG. 9A illustrates an example where the LED indicators are controlled to display that the user has to run (R) for 30 minutes to reach the target. FIG. 9B illustrates an example where the LED indicators are controlled to display that the user has to walk (W) for 110 minutes to reach the target. Similar instructions may be provided with respect to the other intensities, e.g. cycling or doing household chores. Displays of FIGS. 9A and 9B may be displayed alternately such that the user is informed of different options to reach the target. In an embodiment, an aggregation of multiple activity classes and corresponding durations may be displayed, e.g. 20 minutes of running plus 40 minutes of walking. It should be appreciated that the duration to reach the target may also be displayed on the secondary display 500 as a progress of the bar formed by a series of adjacent illuminated LED indicators. The illuminated LED indicators may show activity accumulation thus far, while dimmed LED indicators show the activity that has to be accumulated to reach the target.

As described above, the wrist device 12 may establish a communication link with the portable electronic device 14. The communication link may be employ Bluetooth® technology, for example, but other wireless communication technologies are equally possible. The portable electronic device 14 may be a mobile phone, a tablet computer, a portable digital assistant, a portable music player, etc. The portable electronic device 14 may comprise a thin film transistor (TFT) display or another high resolution display. The resolution may be substantially higher than the resolution of the display(s) of the wrist device 12. Accordingly, the user may employ the higher resolution display to monitor the activity, activity accumulation, and training targets and statistics in greater detail. FIGS. 10A to 18B illustrate some embodiments for configuring the portable electronic device 14 to display high resolution activity statistics.

Figure 10A:
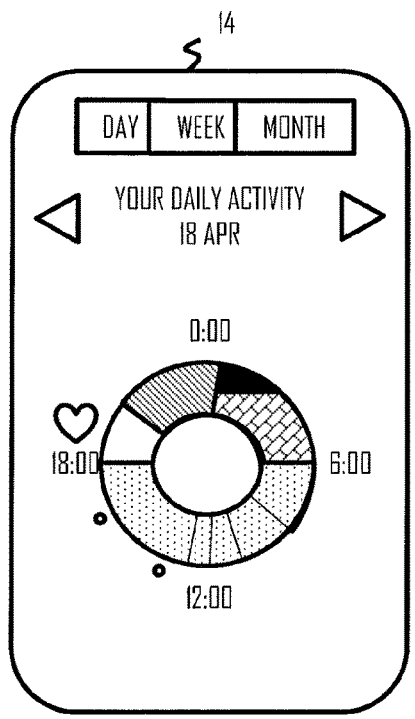
FIGS. 10A to 18B illustrate embodiments related to configuring a portable electronic device to display physical activity of the user.

The portable electronic device 14 may be configured to receive the activity metric(s) from the wrist device 12 and store the activity metric(s) in a memory and/or upload the activity metric(s) to a web server. The activity metric(s) may represent momentary activity and/or activity accumulation. The activity level may be classified in the wrist device 12 and/or in the portable electronic device 14 on the basis of the measurement data, e.g. a higher motion or heart rate may be allocated to a higher activity class and, accordingly, activity accumulation in that class is increased. Referring to FIG. 10A, the portable electronic device 14 may construct a display view from the received activity data. As illustrated in FIG. 10A, the portable electronic device 14 may display accumulation of the activity in each of a plurality of activity classes over a determined time interval. The portable electronic device may form a display comprising a scale adapted to the determined time interval. The time interval may be a determined number of hours such as 12 or 24 hours (a day) or a determined number of days (a week, a month, or a year). The display view may comprise selection components the user may point to select a desired time interval (illustrated by selection components denoted by "day", "week", and "month" in FIG. 10A). The time interval may be determined by a start time and an end time.

In an embodiment, the portable electronic device 14 is configured to receive heart activity measurement data from the wrist device 12.

In an embodiment, the portable electronic device 14 is configured to store and process the received heart activity measurement data to obtain heart activity metrics.

In an embodiment, the portable electronic device 14 is configured to receive motion measurement data from the wrist device 12.

In an embodiment, the portable electronic device 14 is configured to store and process the received motion measurement data to obtain motion activity metrics.

In an embodiment, the portable electronic device 14 is configured to store and process the heart activity measurement data and the motion measurement data to obtain an activity metric based on both the heart activity measurement data and the motion measurement data.

In an embodiment, the portable electronic device 14 is configured to communicate at least one of the heart activity measurement data, the motion measurement data, and the activity metric(s) to a web server.

The portable electronic device 14 may further illustrated in the display view text or image information indicating the currently displayed time interval to the user. Browsing components may be provided to enable the user to browse from a display of one time interval to a display of another time interval, e.g. an adjacent time interval before or after the currently displayed time interval.

Figure 11A:
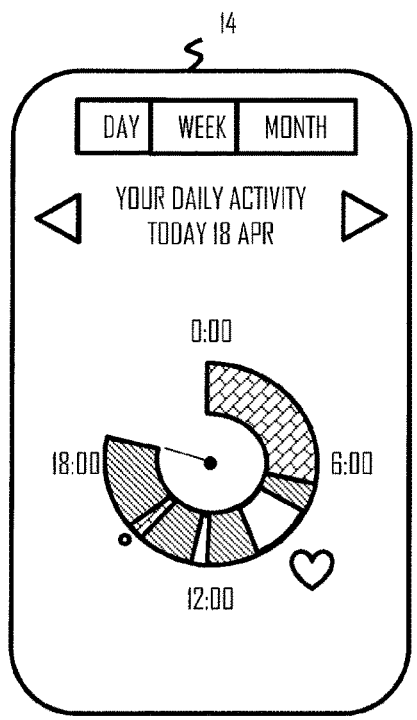
Figure 11B:
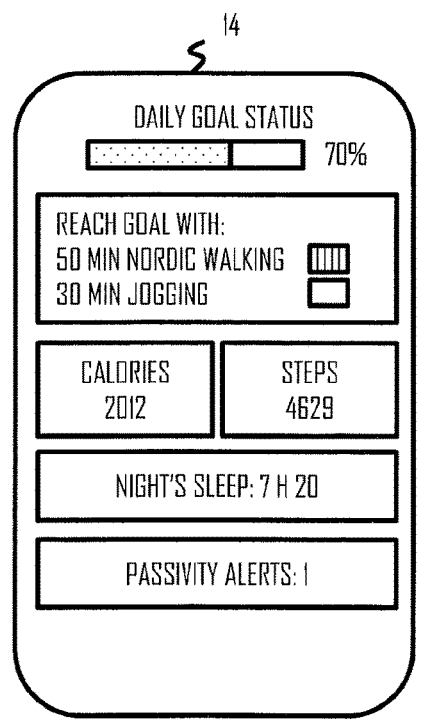

With respect to the display of the activity accumulation, the portable electronic device 14 may display an object which may be a diagram in a form of a figure, a picture, or a geometric shape. The object may be visually complete if the determined time interval has expired, and incomplete if the determined time interval is still running. In FIG. 10A, a geometric shape of an annulus is illustrated and, since the annulus is complete, the time interval (a day of $18^{th}$ April) has expired. FIG. 11A illustrates an incomplete annulus so in that example the time interval is still running. Times of the day, days, or months may be illustrated around the object to help the user in understanding proportions in the object.

The activity accumulation may be illustrated by filling portions of the object according to an activity accumulation distribution during the determined time interval. As described above, the activity accumulation during the time interval may be quantized into a plurality of activity classes, thus acquiring an accumulation sub-interval for each activity class in the time interval. A duration of a sub-interval of an activity class with respect to the time interval indicates the proportion of how much time the user has accumulated activity in that activity class. Portions of the object may then be filled such that an activity class having a longer sub-interval is allocated a bigger portion in the object than an activity class having a shorter sub-interval. Referring to FIG. 10A, each activity class may be assigned a sector in the annulus. Each activity class may be assigned a single, continuous portion which helps the user in determining the length of each sub-interval. The portions of the activity classes may be sorted into the object in an order of increasing or decreasing activity class.

In the embodiment of FIG. 10A, all the activity accumulated in a given activity class is aggregated and displayed in a single portion.

Each portion may be provided with a unique visual coding such that the user is able to distinguish the activity classes. The visual coding may be realized by assigning a unique pattern, filling pattern, or color to each activity class.

As described above, the activity may be measured from motion measurement data and/or heart activity measurement data. In an embodiment, the portable electronic device 14 illustrates in the display view an indicator indicating the type of measurement data used when computing the activity accumulation of a given portion. For example, whenever heart activity measurement data has been used, an icon (such as the heart icon in FIG. 10A) may be displayed in connection with the portion for which heart activity measurement data has been used. In an embodiment, the motion measurement data may be a default type of data used for computing the accumulation so display of a specific indicator indicating that the motion measurement data has been used may be omitted. According to an aspect, a unique visual coding may be provided for each measurement data type, e.g. a pattern or a color.

With respect to displaying the heart icon, a different type of heart icon may be displayed depending on whether the heart activity measurements associated with the activity have been acquired from a heart activity sensor that is internal or external with respect to the wrist device 12. For example, when the wrist device 12 employs an internal heart activity sensor, e.g. a sensor based on optical heart activity measurements, one type of heart icon may be displayed. On the other hand, when the wrist device 12 employs an external heart activity sensor, e.g. a heart rate transmitter attached to the user's chest with a strap, another type of heart icon may be displayed, e.g. a heart surrounded by a strap.

In an embodiment, the wrist device 12 is configured to output an alarm or notification when the user is determined to be excessively inactive. The training program may define an activity pattern for the time interval. The activity pattern may comprise a time distribution of target activity accumulation. For example, the user may be allowed to stay on the lowest activity level in the night, while the lowest activity level may not be allowed during another time interval. If the wrist device 12 detects that the user's activity is on the lowest activity level when it is not allowed, it may be configured to output the alarm or the notification and thus instruct the user to raise activity. The wrist device 12 may also store in the memory a time stamp indicating when the alarm or the notification has been output. This time stamp may be output to the portable electronic device 14 and displayed on the display view as a unique indicator in the timing of the time label (e.g. dots in FIG. 10A). The location of these indicators with respect to the object may thus be determined from the time stamp.

Figure 10B:
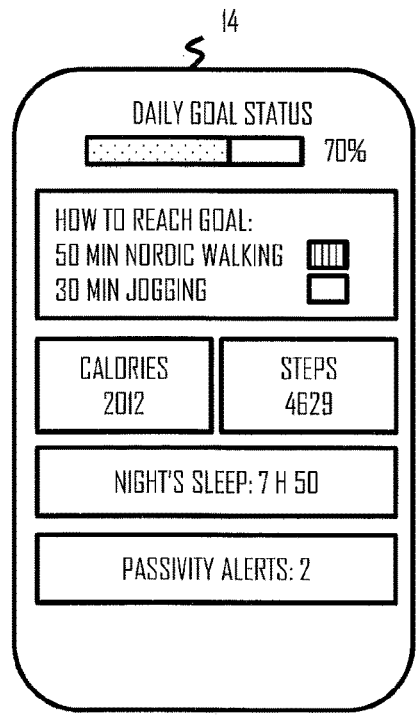

FIG. 10B illustrates another display view. The user may switch from the view of FIG. 10A to the view of FIG. 10B by operating the user interface of the portable electronic device 14, e.g. a swipe gesture on a touch-sensitive display. In FIG. 10B, the portable electronic device 14 illustrates various numeral statistics about the activity within the determined time interval of FIG. 10A. The display view may comprise an accumulation indicator and a target indicator for showing a proportion of activity accumulated during the time interval with respect to a target accumulation of the time interval. The display view may further comprise instructions as how the target may be or may have been reached. This may be computed as described above in connection with FIG. 8 and illustrated in a more graphical manner with the high-resolution display. The display view may further comprise the energy expenditure in terms of expended calories, for example. The energy expenditure may be computed from the motion measurement data and/or the heart activity measurement data, depending on the type of measurement data available at each instant. In an embodiment, the display view further comprises an indication of number of steps or another numerical activity accumulation figure illustrating total motion activity during the time interval. Such a figure may be computed from the motion measurement data. The display view may further comprise a numerical time value indicating the amount of sleep the user has gained during the night. This may be computed by allocating a time interval for the night, e.g. from 10 pm to 8 am, and computing the amount of time the user's activity fulfills sleeping criteria during that time interval. The display view may further comprise a numerical value illustrating the number of passivity alerts output during the determined time interval.

FIG. 11A illustrates an embodiment where the determined time interval is still running. Accordingly, the shape of the object is incomplete. The shape of the object may itself serve as an indicator of the remaining time until the time interval expires, e.g. the degree of (in)completeness of the object serves as such an indicator. For example, if the annulus of FIG. 11A is 75% annular, 25% of the time is still remaining. Furthermore, a time indicator such as a clock pointer may indicate the current time. In an embodiment, a clock is provided at the center of the object. In an embodiment, the annulus represents a 24 hour clock.

In the embodiment of FIG. 11A, the activity metric(s) may be transferred from the wrist device 12 to the portable electronic device 14 in real time or at least regularly at determined time intervals, e.g. with a determined periodicity. In the embodiment of FIG. 11A, the activity may be illustrated in an order of timely occurrence. For example, if the user sleeps from 0 am to 7 am and takes a morning exercise from 8 am to 9 am, the object shows the lowest activity class or a specific sleep indication for the time interval when the user slept and a high activity class between 8 am and 9 am. Accordingly, the displayed time distribution of the activity classes is the same as their occurrence during the time interval.

It should be appreciated that the sorting of activity classes in the display views of 10A and 11A may be reversed, e.g. the order of occurrence view may be displayed even after the time interval has expired and the aggregated activity view may be displayed when the time interval is still running.

In an embodiment, an illustration of each activity class may be displayed in the display view of FIGS. 10A and/or 11A. The illustration may comprise a shape matching the unique coding of each activity class and an icon illustrating the activity level of the activity class. The icon may represent a person sleeping, sitting, standing, walking, or running, depending on the activity class.

Figure 12A:
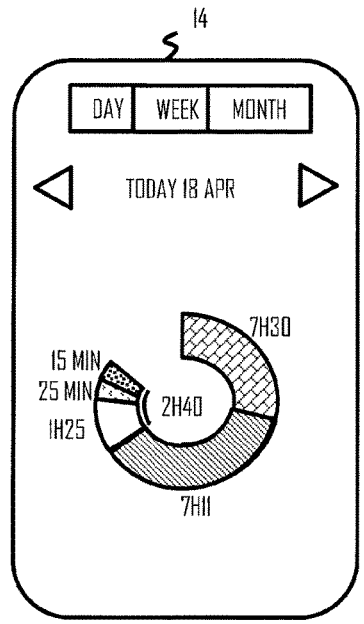
Figure 12B:
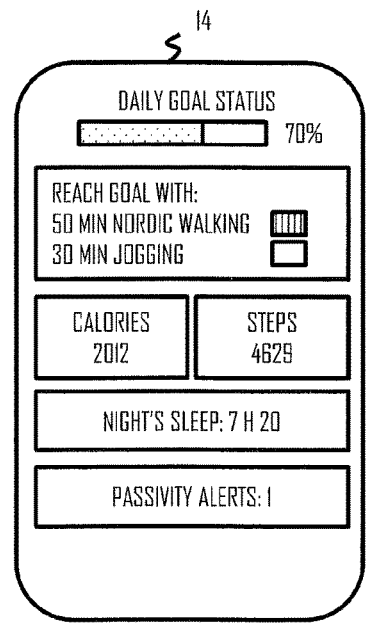

In the embodiments of FIGS. 10A and 11A, the numerical values illustrated next to the object illustrate absolute time values along the time interval. FIG. 12A illustrates an embodiment providing the aggregated view where all the activity accumulated in a given activity class is aggregated into a portion of the object, and the portions are illustrated in an order of increasing activity. A numeric value may be provided in connection with each portion, and the value may represent the duration the user has spent in a corresponding activity class. For example, a value 7H30 beside the lowest activity class in FIG. 12A may represent that the user has slept or stayed still for 7 hours 30 minutes. A numeric value at the center of the object may indicate how much of the time interval is still left. In an embodiment, an aggregate indicator may be displayed to indicate an aggregate duration the user has accumulated activity in multiple activity classes. For example, the indicator may indicate the aggregate duration the user has accumulated activity in a determined number of highest activity classes. In the embodiment of FIG. 12A the aggregate indicator is provided as an arc inside the annulus and next to the three highest activity classes. In this embodiment, the numeric value at the center of the object may indicate as a numeric value the aggregate duration the user has accumulated activity in the three highest activity classes. The numeric value may represent the user's high activity time.

Figure 13A:
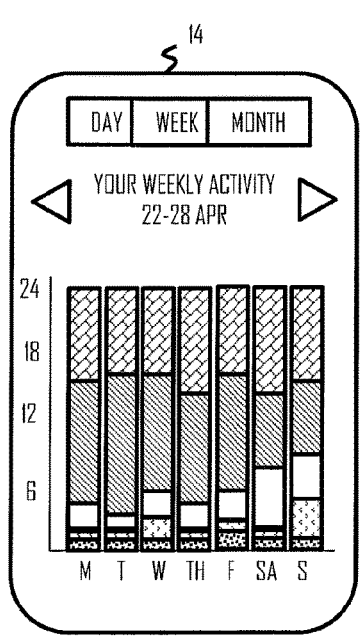
Figure 13B:
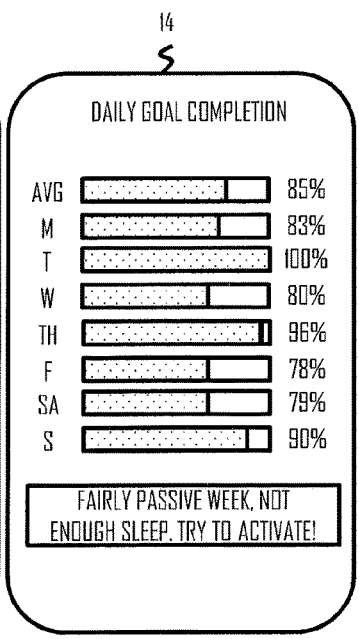

FIG. 13A illustrates a weekly view and using bars as the objects. A single bar may be displayed per day, as illustrated in FIG. 13A, or a single aggregate bar may be displayed to illustrate the activity accumulated during the week. When all the days of the time interval have expired, all the bars may be complete and equal length. If the time interval is still running, one of the bars may have a shorter length and/or one or more bars associated with future days may be omitted from the display. The bars may be filled with portions associated with each activity class and having the unique visual coding. Aggregating and sorting may be used according to the embodiment of FIG. 10A (as shown in FIG. 13A), or the timely based order of occurrence view of FIG. 11A may be used. FIG. 13B illustrates a view to which the user may switch from the view of FIG. 13A by operating the user interface of the portable electronic device 14. The display view of FIG. 13B illustrates the daily activity accumulation with respect to daily targets. The display view of FIG. 13B may further comprise an average daily accumulation within the time interval and with respect to an average daily target. The display view of FIG. 13B may further comprise a verbal summary of the user's performance.

Figure 13C:
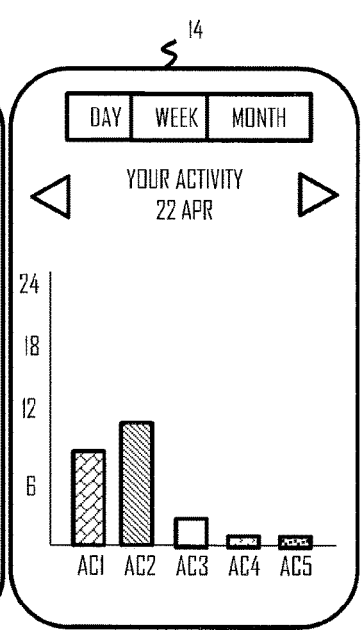

FIG. 13C illustrates a view where one of the bars of FIG. 13A has been exploded into multiple bars such that each portion of the bar of FIG. 13A, i.e. each activity class, is illustrated as a stand-alone bar. This type of view enables better evaluation of the mutual portions of the different activity classes to be performed.

Figure 14A:
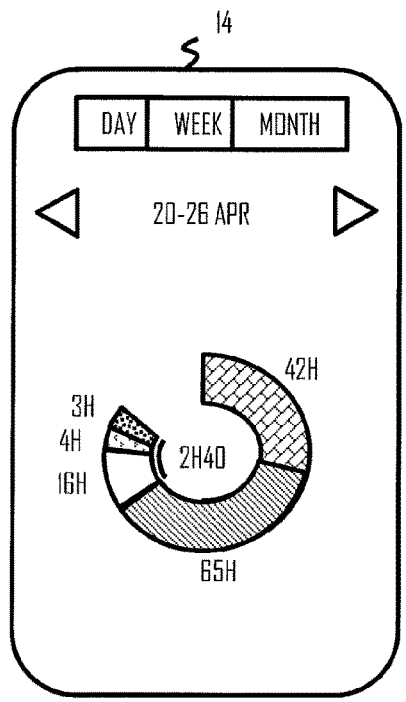
Figure 14B:
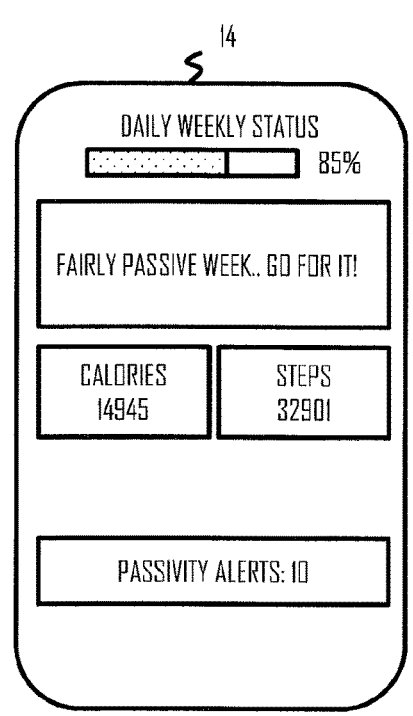

FIG. 14A illustrates the weekly view by using the annulus as the object, and aggregation and sorting as the scheme for illustrating the activity classes. FIG. 14B illustrates a view to which the user may switch from the view of FIG. 14A by operating the user interface of the portable electronic device 14. In the weekly view, this display may provide a performance indicator indicating the accumulated activity with respect to the target and the summary of the performance. Calories and/or steps acquired during the time interval may be displayed, as well as the number of passivity alerts.

In an embodiment, background of the display may change according to the time of the day and/or seasons. For example, a nighttime view may be displayed in the nighttime while a daylight view may be displayed in other time instants.

Figure 15:
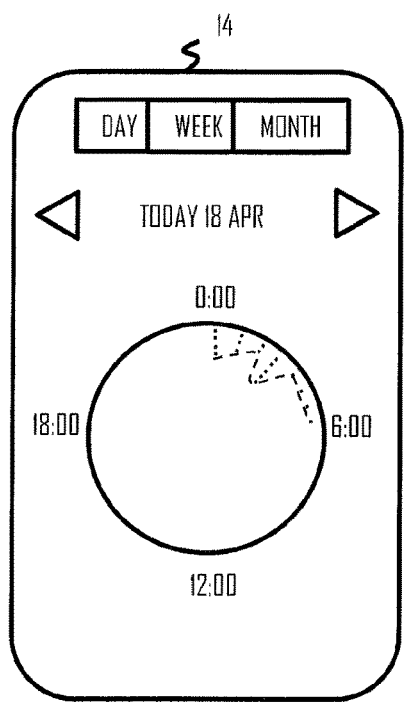
Figure 16:
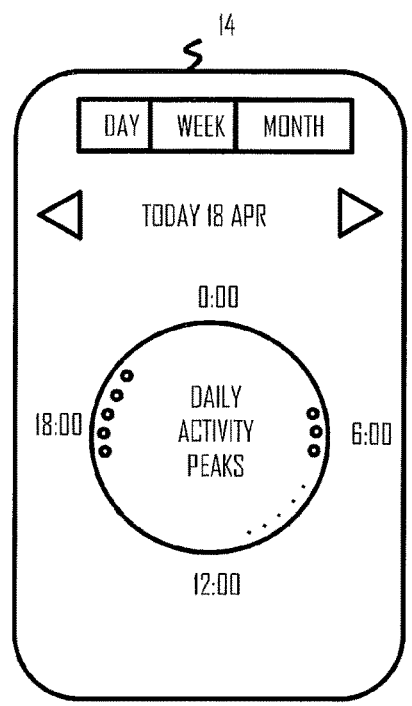

FIG. 15 illustrates an embodiment of the display of the portable electronic device 14 where the object illustrates the accumulated activity as lines that extend from an edge of a circle towards the center of the circle, and the degree of the extension is proportional to the activity accumulated during an observation interval. The observation interval may be a sub-interval of the time interval being displayed. For example, in a daily view the observation interval may be one hour and, after expiry of the time interval, the daily view may comprise 24 lines that extend towards the center. In another embodiment, the lines extend from the center towards the edge of the circle. Instead of lines, bars or even sectors may be used. A line connecting the heads of the lines may be drawn to illustrate the change of the activity accumulation between different observation intervals.

Figure 17A:
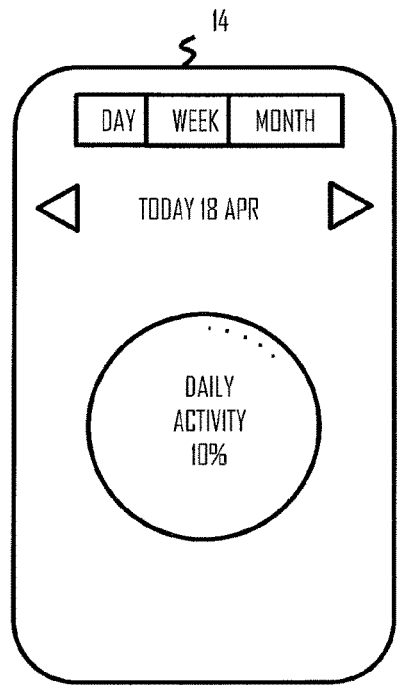

FIGS. 17A to 18B illustrate display views for use when the time interval is running. FIGS. 17A to 18B illustrate embodiments indicating accumulated activity with respect to the target of the time interval as a concatenation of shapes filling a pattern. In the embodiment of FIG. 17A, dots are lit on the display view as the user accumulates the activity and, when the target of the time interval has been reached, the concatenated dots form a complete shape such as a ring. A numerical value of the progress corresponding to the number of displayed dots may also be displayed on the same display view.

Figure 17B:
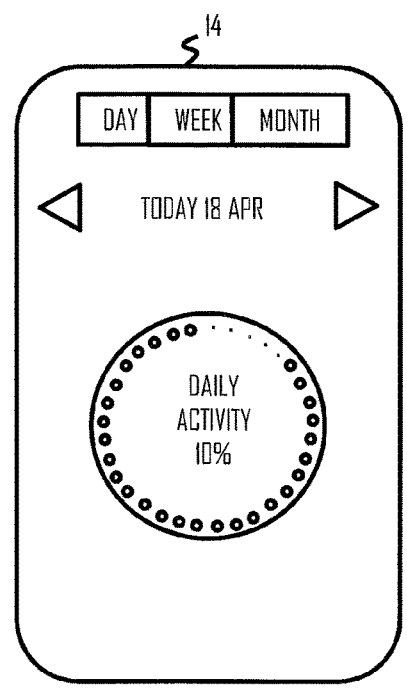

In the embodiment of FIG. 17B, an initial display view at the beginning of the time interval comprises a ring of mini rings. The mini rings will be replaced by dots or filled as the user accumulates activity. The mini rings may be filled in a clockwise order.

Figure 18A:
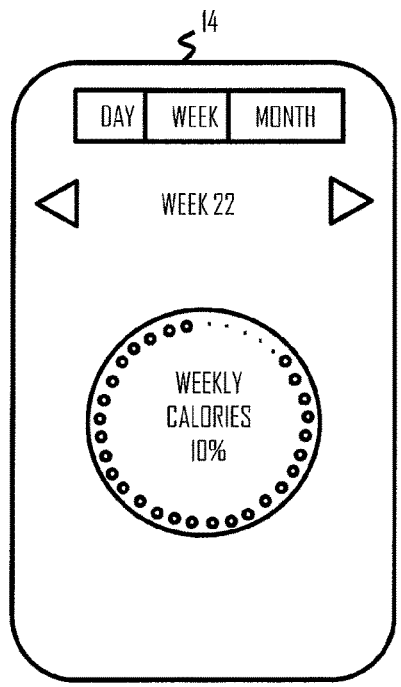
Figure 18B:
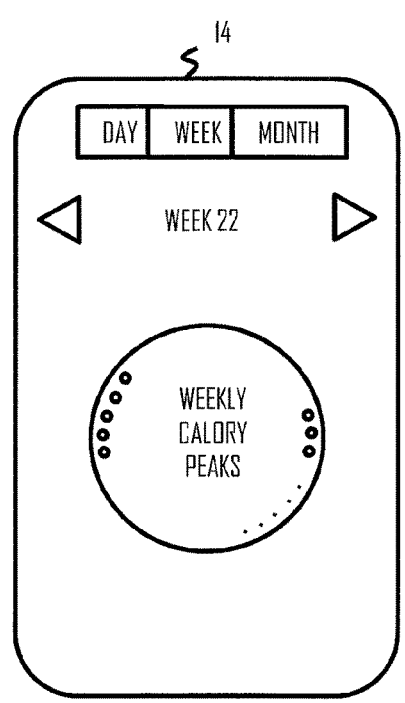

FIGS. 17A and 17B illustrate daily views but similar view may be provided for other time intervals, e.g. a week or a month. FIG. 18A illustrates a progress indicator similar to that of FIG. 17B but, instead of a daily activity, weekly energy expenditure is monitored. The activity may be measured through the accumulation in the activity classes or through another metric such as the energy expenditure.

Figure 19:
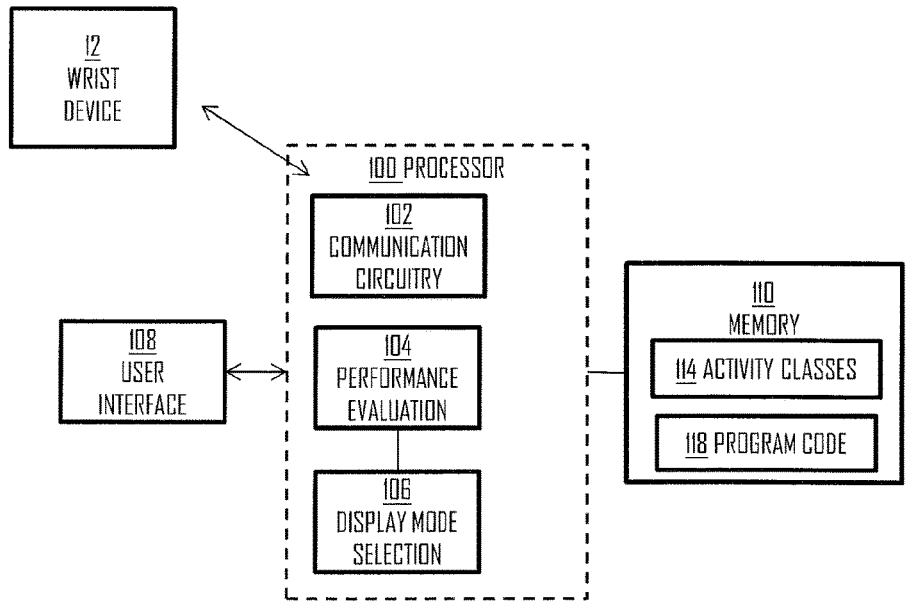
FIGS. 19 and 20 illustrate block diagrams of apparatuses according to some embodiments of the invention.

FIG. 19 illustrates a block diagram of a structure of an apparatus according to an embodiment of the invention. The apparatus may be applicable to or comprised in the portable electronic device 14. The apparatus may comprise at least one processor 100 or processing circuitry and at least one memory 110 including a computer program code 118, wherein the at least one memory and the computer program code are configured, with the at least one processor, to cause the apparatus to carry out the functions described above in connection with the portable electronic device. The processor 100 may comprise a communication circuitry 102 as a sub-circuitry configured to handle the wireless connection with the wrist device. The communication circuitry 102 may be configured to establish, maintain, and terminate wireless connections with the wrist device 12 and transfer data over the connections. For example, the measurement data and/or the activity metrics may be transferred through the communication circuitry 102 and stored in the memory 110 as activity data. The activity data may comprise at least one of the following: the heart activity measurement data, the motion measurement data, and the activity metric(s) computed by the wrist device 12 on the basis of the heart activity measurement data and/or the motion measurement data. In an embodiment, the portable electronic device 14 receives raw measurement data as the activity data from the wrist device 12 and computes the activity metric(s) from the raw measurement data. In other embodiments, the portable electronic device 12 receives the activity metric(s) as computed by the wrist device. The portable electronic device may compute further activity metric(s) from the received activity metric(s), e.g. energy expenditure from the activity accumulation.

The processor 100 may further comprise a performance evaluation module 104 configured to process the received activity data. The performance evaluation module may retrieve activity class definitions 114 from the memory 110 and compute activity accumulation in each activity class within a determined time interval. Definitions of the time interval may be received from the user through a user interface 108 of the apparatus. The definitions of the time interval may be received on the basis of the user selecting a desired display view by operating the user interface, e.g. any one of the display views of FIGS. 10A to 18B. The performance evaluation module 104 may compute further metrics from the measurement data or, if it receives the metrics from the wrist device 12, it may simply retrieve the metrics from the memory 110 to which the communication circuitry 102 has stored the metrics. Such further metrics may comprise at least one of the following: an energy expenditure metric, a step count, an estimate of remaining activity accumulation to reach a target, a training load indicator indicating physical training load caused by the activity, and a metric indicating the user's performance in terms of accumulated activity with respect to the target.

The processor 100 may further comprise a display mode selection module 106 configured to control a display screen of the user interface 108 to display the display contents according to any one of the embodiments described above in connection with FIGS. 10A to 18B. The display mode may be selected according to the user input, and the display mode selection module 106 may map the metric(s) computed by the performance evaluation module 104 to the selected display mode. For example, if the performance evaluation module 104 has computed the activity accumulation within the determined time interval and the selected display mode is the one illustrated in FIG. 17A, the display mode selection module 106 may map the computed activity accumulation with respect to an activity target of the time interval and then control the display screen to provide a display view illustrating a corresponding number of dots representing the activity accumulation with respect to the activity target.

In an embodiment, the apparatus applicable to the portable electronic device 14 comprises the communication circuitry 102 configured to establish a wireless communication connection with the communication circuitry of the wrist device, a display screen, and at least one processor 100 configured to receive heart activity measurement data and motion measurement data from the wrist device 12 through the communication circuitry 102, to process the heart activity measurement data and motion measurement data, and to cause the display screen to display the processed heart activity measurement data and motion measurement data. The processor may be configured to carry out any one of the above-described embodiments of the portable electronic device 14.

Figure 20:
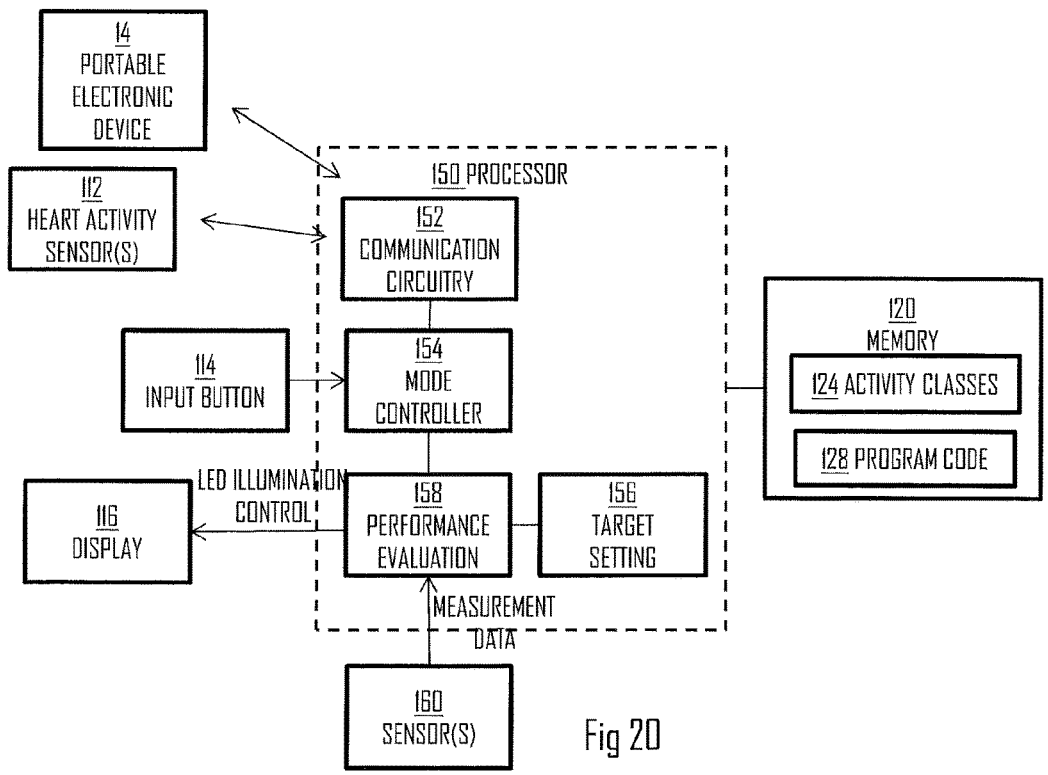

FIG. 20 illustrates a block diagram of an apparatus applicable to or comprised in the wrist device 12. The apparatus may comprise at least one processor 150 or processing circuitry and at least one memory 120 including a computer program code 128, wherein the at least one memory and the computer program code are configured, with the at least one processor, to cause the apparatus to carry out the functions described above in connection with the wrist device 12. The processor 150 may comprise a communication circuitry 152 as a sub-circuitry configured to handle the wireless connection with the portable electronic device 14 and one or more sensor devices 112. The sensor device(s) may comprise at least one heart activity sensor. The communication circuitry 152 may be configured to establish, maintain, and terminate wireless connections with the sensor device(s) 112 and receive measurement data over the connections. The communication circuitry 152 may be configured to establish, maintain, and terminate wireless connections with the portable electronic device 14 and transmit activity metric(s) computed in the wrist device and/or the measurement data to the portable electronic device 14. The communication circuitry 152 may further receive training target(s) and/or other configuration parameters from the portable electronic device 14.

The apparatus may further comprise a mode controller 154 configured to change the operational mode of the apparatus. The operational mode may be changed according to the embodiment described above in connection with FIG. 4, for example. Accordingly, when the mode controller 154 receives an input through the input button 114 of the user interface, the mode controller 154 may start a process for changing the operation mode from motion measurements to heart activity measurements, for example. When switching from the motion measurements to the heart activity measurements, the mode controller 154 may output a control signal to the communication circuitry 152 to establish a wireless link to the heart activity sensor(s). Upon receiving a signal of completed establishment of the wireless link to at least one heart activity sensor from the communication circuitry 152, the mode controller may change the operational mode and control a performance evaluation circuitry 158 to start using heart activity measurement data received through the communication circuitry 152 in the computation of the activity metric(s). On the other hand, upon receiving an input from the input button 114 to change from the heart activity measurements to the motion measurements or upon receiving a notification from the communication circuitry that the wireless link to the heart activity sensor(s) has been terminated, the mode controller 154 may initiate the motion measurement mode and control the performance evaluation circuitry 158 to perform the activity metric computation from motion measurement data received from one or more motion sensors 160 comprised in the apparatus and/or from one or more external motion sensors.

In an embodiment where the sensor(s) 160 of the apparatus comprise a heart activity sensor, the mode controller 160 may activate the internal heart activity sensor without connecting to the external heart activity sensor upon receiving the input to change to the heart activity measurements. The internal heart activity sensor may be based on optical heart rate sensing, for example.

The performance evaluation circuitry 158 may compute the activity metric(s) in the above-described manner. The performance evaluation circuitry 158 may retrieve from the memory definitions of activity classes 124 and map the computed activity metrics into the activity classes. The performance evaluation circuitry 158 may further compute activity accumulation in each activity class. The performance evaluation circuitry 158 may further receive one or more performance targets from a target setting circuitry 156. The target setting circuitry may determine one or more activity targets for a determined time interval and output the activity target(s) to the performance evaluation circuitry 158. The activity target(s) may be retrieved from the memory or computed according to the previous performance computed by the performance evaluation circuitry 158. For example, the memory 120 may store initial activity targets but, if an activity history indicates that the user has exceeded previous training targets, the target setting circuitry may adapt the initial targets by raising them. Similarly, if the activity history indicates that the user has not reached the previous training targets, the target setting circuitry 156 may adapt the initial targets by lowering them.

Upon determining the activity performance with respect to the targets, the performance evaluation circuitry 158 may control a display 116 of the apparatus to illuminate one or more LED indicators in the above-described manner (see FIGS. 5A, 5B, 9A, and 9B).

According to an aspect, there is provided an activity monitoring system comprising the apparatus of FIG. 19 and the apparatus of FIG. 20.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor (s)/software including digital signal processor(s), software, and at least one memory that work together to cause an apparatus to perform specific functions; and (c) circuits, such as a microprocessor(s) or a portion of a microprocessor (s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in FIGS. 4 to 8 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to the performance monitoring systems described above. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A system that monitors user activity, the system comprising:

a wrist device comprising a curved body and an electronic circuitry supported by the body, the electronic circuitry comprising a first set of light emitting diodes arranged in a matrix form and forming a display unit, at least one motion sensor configured to measure physical motion caused by a user to the wrist device, a heart activity sensor based on optical heart activity sensing, and at least one processor configured to acquire motion measurement data from the at least one motion sensor, to process the motion measurement data into a motion activity metric, and to cause the display unit to display the motion activity metric, wherein the at least one processor is further configured to acquire heart activity measurement data from the heart activity sensor, to process the heart activity measurement data into a heart activity metric, and to cause the display unit to display the heart activity metric, and wherein the at least one processor is further configured to estimate a sleep index, the sleep index characterizing a user's sleep quality and sleep time by using an activity sensor comprising at least one of said heart activity sensor and said at least one motion sensor; and wherein the processor of the wrist device is further configured to determine an energy expenditure target, to determine at least one training intensity as a momentary training intensity from at least one of the motion measurement data and the heart activity measurement data, to compute from the momentary training intensity and a difference between the energy expenditure target and the energy expenditure accumulation value, at least one time duration needed to exercise with the determined momentary training intensity to reach the energy expenditure target, and to cause the first set of light emitting diodes to display the determined at least one time duration in connection with an indicator of a corresponding training intensity.

2. The system of claim 1, wherein the communication circuitry of the wrist device is configured to establish a wireless communication connection with an external heart activity sensor, and wherein the at least one processor of the wrist device is configured to acquire the heart activity measurement data from the heart activity sensor through the communication circuitry.

3. The system of claim 2, wherein the external heart activity sensor is configured to transmit signal at predetermined signal strength, and the wrist device comprises a communication circuitry configured to measure signal strength of the external heart activity sensor, to compare the signal strength with a predetermined threshold, and to pair with the external heart activity sensor whose signal strength is above the predetermined threshold.

4. The system of claim 1, wherein the wrist device comprises a Bluetooth communication circuitry.

5. The system of claim 1, wherein the processor of the wrist device is configured to automatically change from a motion monitoring mode to a heart activity monitoring mode when the communication circuitry is connected to an external heart activity sensor.

6. The system of claim 1, the wrist device further comprising an internal heart activity sensor configured to measure heart activity of the user from a wrist, and wherein the at least one processor of the wrist device is configured to acquire the heart activity measurement data from the internal heart activity sensor.

7. The system of claim 1, wherein the wrist device further comprises a second set of light emitting diodes forming a second display of the wrist device and wherein the processor is configured to cause the first set of light emitting diodes to display one of the motion activity metric and the heart activity metric and the second set of light emitting diodes to display the other of the processed heart activity measurement data and the activity metric.

8. The system of claim 1, wherein the processor of the wrist device is further configured to map the motion measurement data and the heart activity measurement data to a common scale through an energy expenditure equivalent.

9. The system of claim 1, wherein the processor of the wrist device is configured to determine the at least one training intensity from a reference training intensity stored beforehand in a memory of the wrist device.

10. The system of claim 1, wherein the wrist device comprises a communication circuitry configured to provide the wrist device with wireless communication capability, the system further comprising a portable electronic device comprising a communication circuitry configured to establish a wireless communication connection with the communication circuitry of the wrist device, a display screen, and at least one processor configured to receive heart activity measurement data and motion measurement data from the wrist device through the communication circuitry, to process the heart activity measurement data and motion measurement data, and to cause the display screen to display the processed heart activity measurement data and motion measurement data.

11. The system of claim 10, wherein the processor of the portable electronic device is configured to determine activity accumulation within a determined time interval and to cause the display screen to display a scale indicating the determined time interval and at least one indicator indicating the determined activity accumulation within the determined time interval.

12. The system of claim 11, wherein the processor is configured to compute activity accumulation from the motion measurement data and from the heart activity measurement data and to cause the display screen to display an indicator indicating whether the displayed activity accumulation associated with said at least one indicator is based on the motion measurement data or the heart activity measurement data.

13. The system of claim 11, wherein the scale is represented by an object such that when the time interval has expired, the object is visually complete, and when the time interval is still running, the object is visually incomplete.

14. The system of claim 10, wherein the processor of the portable electronic device is further configured to classify the heart activity measurement data and/or motion measurement data into a plurality of activity classes, determine activity accumulation in each of the plurality of activity classes, and cause the display screen to display the activity accumulation in each of the plurality of activity classes within the determined time interval.

15. The system of claim 1, wherein the activity sensor comprises the at least one motion sensor, and wherein the at least one processor is configured to determine the sleep time as a continuous time when motion measurement data received from the at least one motion sensor indicates user's physical activity below a predefined sleep threshold.

16. The system of claim 1, wherein the at least one processor is configured to divide the sleep time to a number of time periods of a predefined length, and to estimate the sleep quality on the basis of a relative number of detected deep sleep time periods compared with the number of time periods.

17. The system of claim 16, wherein the activity sensor comprises the at least one motion sensor, and wherein a time period is determined to be a deep sleep time period when motion measurement data received from the at least one motion sensor indicates user's physical activity below a predefined deep sleep threshold.

18. The system of claim 1, wherein the at least one processor is configured to divide the sleep time to a number of time periods of a predefined length, use a deep sleep threshold to detect which one or more of the number of time periods are associated with restless sleep, and to estimate the sleep quality on the basis of a relative number of detected restless sleep time periods compared with the number of time periods.

19. A system that monitors user activity, the system comprising:
a wrist device comprising a curved body and an electronic circuitry supported by the body, the electronic circuitry comprising a first set of light emitting diodes arranged in a matrix form and forming a display unit, at least one motion sensor configured to measure physical motion caused by a user to the wrist device, a heart activity sensor based on optical heart activity sensing, and at least one processor configured to acquire motion measurement data from the at least one motion sensor, to process the motion measurement data into a motion activity metric, and to cause the display unit to display the motion activity metric, wherein the at least one processor is further configured to acquire heart activity measurement data from the heart activity sensor, to process the heart activity measurement data into a heart activity metric, and to cause the display unit to display the heart activity metric, wherein the at least one processor is further configured to estimate a sleep index, the sleep index characterizing a user's sleep quality and sleep time by using an activity sensor comprising at least one of said heart activity sensor and said at least one motion sensor, wherein the at least one processor is configured to divide the sleep time to a number of time periods of a predefined length, the predefined length being a length of a deep sleep time period and use a deep sleep threshold to detect which one or more of the number of deep sleep time periods are associated with deep sleep to estimate the sleep quality on the basis of a number of detected deep sleep time periods relative to the number of time periods and display the sleep index as a percentage of the detected deep sleep time period relative to the number of time periods.

20. A system that monitors user activity, the system comprising:
a wrist device comprising a curved body and an electronic circuitry supported by the body, the electronic circuitry comprising a first set of light emitting diodes arranged in a matrix form and forming a display unit, at least one motion sensor configured to measure physical motion caused by a user to the wrist device, a heart activity sensor based on optical heart activity sensing, and at least one processor configured to acquire motion measurement data from the at least one motion sensor, to process the motion measurement data into a motion activity metric, and to cause the display unit to display the motion activity metric, wherein the at least one processor is further configured to acquire heart activity measurement data from the heart activity sensor, to process the heart activity measurement data into a heart activity metric, and to cause the display unit to display the heart activity metric, wherein the at least one processor is further configured to estimate a sleep index, the sleep index characterizing a user's sleep quality and sleep time by using an activity sensor comprising at least one of said heart activity sensor and said at least one motion sensor, wherein the at least one processor is configured to divide the sleep time into a total number of time periods of a predefined length, the predefined length being a length of a deep sleep time period, use a deep sleep threshold to detect which one or more of the number of deep sleep time periods are associated with restless sleep, estimate the sleep quality on the basis of a number of detected restless sleep time periods relative to the total number of time periods and display the sleep index as a percentage of the detected restless sleep time period relative to the number of time periods.

\* \* \* \* \*